United States Patent [19]
Galeotti et al.

[11] Patent Number: 5,432,082
[45] Date of Patent: Jul. 11, 1995

[54] EXPRESSION AND SECRETION VECTOR IN YEASTS, USEFUL FOR PREPARING HETEROLOGOUS PROTEINS

[75] Inventors: Cesira Galeotti, Siena; Emanuela Palla, Montecatini Terme; Giovanni Raugei; Giuliano Bensi, both of Florence; Maria L. Melli, Siena, all of Italy

[73] Assignee: Sclavo, S.p.A., Siena, Italy

[21] Appl. No.: 69,455

[22] Filed: Jun. 1, 1993

Related U.S. Application Data

[63] Continuation of Ser. No. 654,069, Feb. 11, 1991, abandoned, which is a continuation of Ser. No. 69,329, Jul. 2, 1987, abandoned.

[30] Foreign Application Priority Data

Jul. 11, 1986 [IT] Italy .................................. 21106/86

[51] Int. Cl.⁶ ...................... C12N 15/70; C12N 15/81; C12N 19/25
[52] U.S. Cl. .......................... 435/252.33; 435/255.21; 435/320.1; 435/69.52; 935/28; 935/48
[58] Field of Search ............... 435/320.1, 69.52, 172.3, 435/252.8, 255, 256, 252.33, 255.21; 935/28, 41, 43, 48, 60

[56] References Cited

PUBLICATIONS

Baldari, C., et al., (1987) Embo J. 6(1), 229–234.
Chang, C. N. et al., (1986) Mol. Cell. Biol. 6(5), 1812–1819.
Jigami, Y., et al., (1986) Gene 43, 273–279.
Guarente et al., (1982) Proc. Natl. Acad. Sci. U.S.A. 79, 7410–7414.
Stark, M. J. R., et al., (1984) Nucl. Acids Res 12(15), 6011–6024.
Stark, M. J. R., et al., (1986) Embo J. 5(8), 1995–2002.
Innis, M. A., in Yeast Genetic Engineering, eds., Barr, et al., (Butterworths, Boston) Chap. 12 pp. 233–246.
Stark, M. J. R., et al., (1990) Yeast 6, 1–29.
Auron, P. E., et al., (1984) Proc. Natl. Acad. Sci. U.S.A. 81, 7907–7911.
March et al., Nature, V. 315, pp. 641–647 (1985).

*Primary Examiner*—Charles L. Patterson, Jr.
*Attorney, Agent, or Firm*—Hedman, Gibson & Costigan

[57] ABSTRACT

The invention provides an expression and secretion vector in yeasts which is useful for preparing heterologous proteins, comprising a synthetic oligonucleotide which directs the secretion of the heterologous protein wherein the synthetic oligonucleotide is positioned between the inducible hybrid promoter GAL-CYC and a multiple-site polylinker followed by the signals of transcription termination recognized by the RNA polymerase of the yeasts. The invention includes a hybrid plasmid obtained by cloning in one of the restriction sites of the polylinker of the vector, the DNA sequence which codes for a heterologous protein. A process is also described for the preparation of heterologous proteins which comprises cultivating in a suitable culture medium a yeast transformed with the hybrid plasmid and recovering from the culture medium the resulting heterologous proteins. The recovered proteins include hormones, lymphokines, viral antigens or immunogens useful in the therapeutical and diagnostic field.

7 Claims, 4 Drawing Sheets

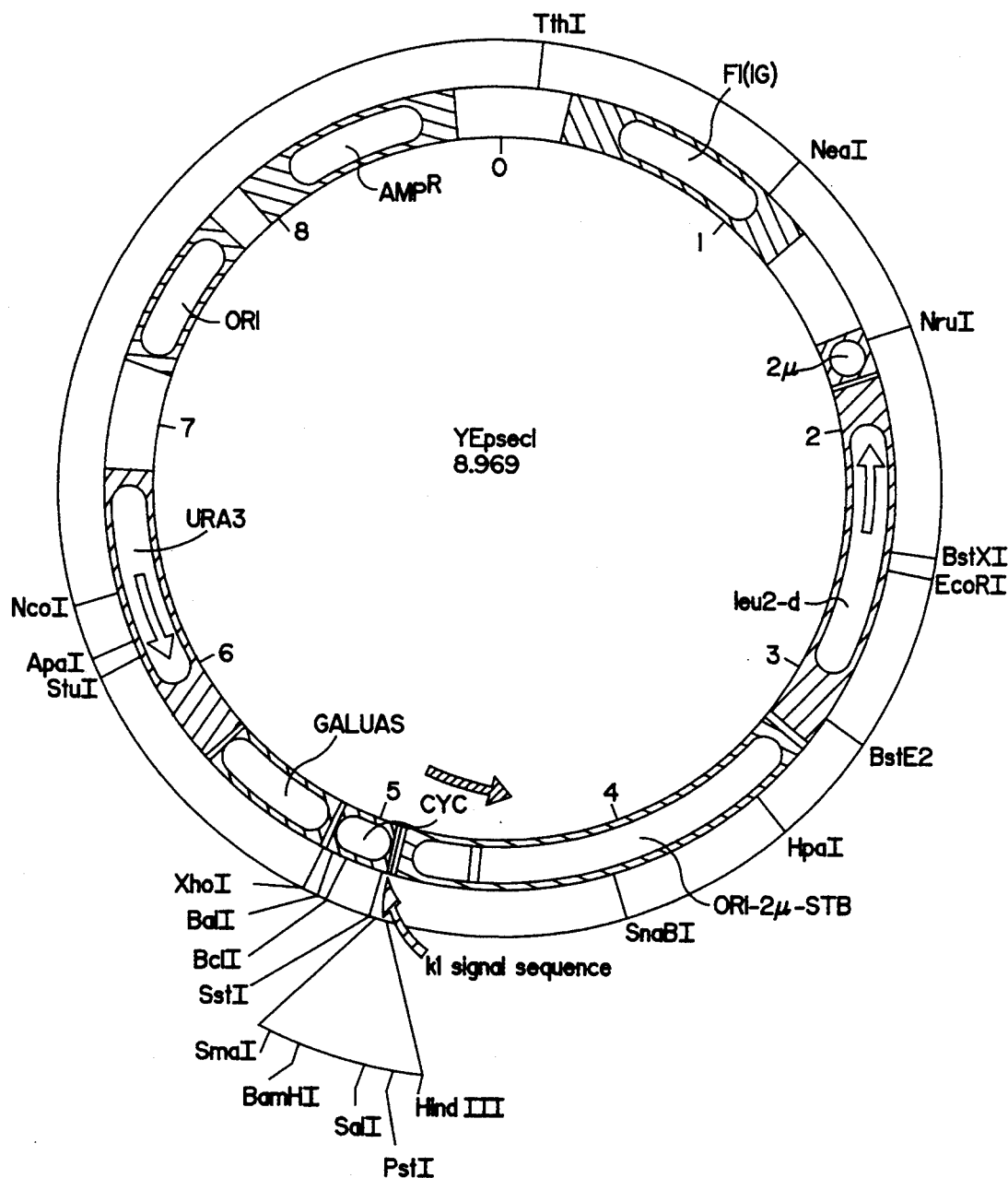
FIG. IB

EXPRESSION AND SECRETION VECTOR IN YEASTS, USEFUL FOR PREPARING HETEROLOGOUS PROTEINS

This application is a continuation of application Ser. No. 07/654,069, filed Feb. 11, 1991, now abandoned, which was a continuation of application Ser. No. 07/069,329, filed Jul. 2, 1987, which is now abandoned.

The present invention relates to an expression and secretion cloning vector in yeasts, useful for preparing heterologous proteins.

The invention relates furthermore to a hybrid plasmid obtained by means of the union of said cloning vector with a DNA sequence which codes for a heterologous protein, and to a process for the preparation of said heterologous protein, which comprises cultivating, in a suitable culture medium, a yeast transformed by means of said hybrid plasmid.

The recent developments in the field of genetic engineering made it possible to prepare heterologous proteins by means of a process comprising the building, by means of recombinant DNA techniques, of a hybrid plasmid containing the gene coding for said protein, introducing said hybrid plasmid into host organisms, and finally cultivating the so-transformed organisms in a suitable culture medium for the purpose of obtaining the protein coded by the heterologous gene.

In general, the heterologous proteins have been prepared heretofore by using, as the host organisms, the bacteria, in that their regulation systems were known.

However, the use of bacteria in said processes causes various problems to occur, such as, e.g., those deriving from the production of enterotoxins, and from the limited availability of strains for use in industrial-type processes.

From the above, there is a need for having available host organisms which do not show the problems of the prior art, such as the yeasts, which, by being eucaryotic organisms, show a greater affinity for mammals, and, differently from bacteria, do not produce enterotoxins, and have been long used in fermentation processes of industrial type.

However, for it to be possible for a yeast to be used as the host cell, it is necessary to have available cloning vectors which are stably kept inside the cells, and which contain regulation signals which make it possible for the cloned heterologous gene to be sufficiently expressed, and the product to be secreted into the culture medium.

From the technical and patent literature, processes are known for the building of expression and secretion vectors in the yeasts, which use regulatory sequences obtained from genes isolated from yeasts. In particular, vectors were built for the secretion of homologous and heterologous proteins, by using leader peptides involved in the secretion of the α factor and of the killer toxin of *Saccharomycer Cerevisiae* (*S. Cerevisiae*). However, said vectors, used in the preparation of human interferon (Singh et al., Nucl. Acids Res., 12, 8927–8938, 1984) and of murine interleukin IL-2 (Miyajima et al., Gene, 37, 155–161, 1985), give rise to a particular secretion of synthesized protein.

In fact, both the α factor and the killer toxin of *S. Cerevisiae* have a leader peptide completely different from those typical for multicellular organisms.

Recent investigations carried out on *Kluyveromces lactis* (*K. lactis*) yeast demonstrated that the killer strains belonging to this species secrete a toxin which is structurally and functionally different from the killer toxin of *S. Cerevisiae* (Sugisaki, Y. et al., 1983, Nature 304, 464–466).

Said toxin constitutes two sub-units, and is secreted in the culture medium as a glycoprotein. At a later time, Stark et al. (Nucl. Acids Res., 12, 6011–6030, 1984), on the basis of the study carried out on the nucleotidic sequence of the gene coding for the toxin of *K. lactis*, hypothesized that its secretion could be directed by a 16-aminoacid long leader peptide, whose structure was similar to that of the leader peptides of procaryotes and eucaryotes.

Even if the presence of the regulation systems can be supposed, it is however not possible to predict whether such systems, used in the building of cloning vectors, are endowed with the capability of performing their functions.

A cloning vector has now been found, which makes it possible to achieve an efficient expression and secretion of heterologous proteins in yeasts.

A purpose of the present invention is therefore an expression and secretion cloning vector in yeasts, useful for the preparation of heterologous proteins, wherein the secretion of the heterologous proteins synthesized is directed by a synthetic oligonucleotide, positioned between an inducible hybrid promoter, and a multiple-site polylinker, followed by the signals of transcription termination recognized by the RNA-polymerase of yeasts.

Another purpose of the present invention is a hybrid plasmid obtained by means of the union of said cloning vector and a DNA sequence coding for a heterologous protein, wherein said sequence is inserted in one of the restriction sites of the polylinker placed downstream the synthetic oligonucleotide.

A further purpose of the present invention is a process for the preparation of heterologous proteins, which comprises cultivating, in a suitable culture medium, a yeast transformed with said hybrid plasmid.

A still further purpose of the present invention is the use of the so-obtained heterologous proteins in the diagnostic and therapeutical fields.

Other purposes of the invention shall be clear to those skilled in the art from the following disclosure.

In accordance with the above, according to the present invention a secretion vector was built by inserting between the restriction sites SstI and KpnI of the expression vector pEMBLyex2 placed downstream of an inducible hybrid promoter, the synthetic oligonucleotide which codes for the hypothetical leader peptide of the killer toxin of *K. lactis*.

In particular, said oligonucleotide comprises the coding section for 16 aminoacids of the amino-end of the killer toxin from the initiator methionine to the presumed site of the cleavage signal of endopeptidase Val-Gln-Gly (D. Perlman et al., J. Mol. Biol. 167, 391–409, 1983).

Said synthetic oligonucleotide is positioned between the inducible promoter (GAL-CYC) and the multiple-site polylinker of p-EMBL18 vector (L. Dente et al., DNA Cloning, Vol. I, IRL Press, London, U.K., pages 101–107, 1985). followed by the signals of transcription termination (3' end of FLP flip flop combination gene of 2 μm plasmid) of pEMBLyex2.

In particular, in said polylinker six individual recognition sites for the restriction endonucleases are present (SmaI, XmaI, BamHI, SaII, PstI, HindIII), which allow the insertion, downstream the synthetic oligonucleotide, of DNA sequences coding for interesting proteins, such as lymphskines, hormones, viral antigens and immunogens.

The secretion vector according to the present invention, indicated as YEsec1, contains furthermore the necessary sequences for the selection and replication in E. coli, as well as the necessary elements for the selection and episomal replication in S. cerevisiae.

According to the present invention, the expression vector pEMBLyex2, the structure of which is shown in FIG. 1A and in Example 1, contains two blocks obtained from yeasts and the necessary sequences for the selection and replication in E. coli. The first block, which determines the episomal replication and the number of plasmid copies, derives from pJBD219 plasmid (Beggs, J.D., 1978, Nature 275, 104–109) and comprises the NdeI-StuI fragment of 3,220 base-pairs containing leu2-d, 2 μm STB and ORI portions of pJBD219. This fragment comprises, furthermore, a small portion of the 3' end of FLP gene of 2 μm plasmid containing the signals of termination of transcription and polyadenylation.

The second block corresponds to HindIII-BamHI fragment of G2 plasmid (Guarente L., 1983, Methods Enzymol., 101, 181–191) and contains the URA 3 gene and the signals which induce the transcription in the polylinker during the growth of the strains transformed with said vector in a medium containing galactose as the only carbon source. The capability of YEpsec1 to direct the expression and secretion of a heterologous gene was verified by cloning, in BamHI site of the polylinker situated immediately downstream the synthetic oligonucleotide of YEpsec1, the cDNA coding for aminoacids 121–269 of human interleukin 1β.

The so-obtained hybrid plasmid, YEpsec1-hI1β, was then used for transforming cells of Saccharomyces cerevisiae, preferably S. cerevisiae S150-2B.

The so-transformed cells, hereinafter named ThI1, were then cultivated, according to general techniques known from the prior art, in a culture medium, containing, as its only carbon source, either galactose or ethanol.

The electrophoretic analysis of the supernatants and of the whole cellular extracts of ThI1 and Tsec1, transformed with the vector YEpsec1 lacking the DNA of human interleukin 1β, show the presence of a protein of about 22,000 daltons in the supernatant of ThI1 cells (line C, FIG. 2), grown on galactose. The S. cerevisiae strain S 150-2B was transformed with YE psec1 and YE psec1-h11 to produce the transformants Tsec1 and ThI1, respectively.

Furthermore, the immunoblotting analysis of said protein in the supernatant and in the cellular extracts of ThI1 cells cultivated in the presence of galactose shows a complete secretion of this protein in the culture medium. By assuming that the secreted protein is recombinant IL-1β, its molecular weight should be about 17,000 daltons.

In as much as IL-1β contains in its sequence a potential site of glycosylation (Asn-Cys-Thr) at the amino-end, the discrepancy in molecular weight could be due to the presence of oligosaccharides bound to the amino group. Hence, according to the present invention, the secreted protein was digested with endoglycosidase H and the digestion product was than analysed again by gel-electrophoresis.

The results shown in FIG. 3 illustrate in fact that, after treatment with endoglycosidase H, the band corresponding to 22,000 daltons disappears and, as expected, a new band of 17,000 daltons appears.

This result was furthermore confirmed by means of the analysis of the supernatants of ThI1 cells grown in a medium containing galactose and tunicamycin, a glycolysation inhibitor.

According to the present invention, the sequence of the nine aminoacidic radicals from the amino end of the secreted protein was determined.

Said sequence (Ser-Leu-X-X-Thr-Leu-Arg-Asp-Ser) results are in agreement with that specified from the 5' end of cDNA of IL-1β (Auron et al., 1984, Proc. Natl. Acad. Sci. USA, 81, 7907–7911) cloned in YEpsec1.

Furthermore, it does not show the presence of any of the three aminoacids coded by the sequence of the polyinker positioned between the synthetic oligonucleotide and the DNA of IL-1β.

This indicates that the cleavage of the leader peptide takes place between the last one of the 3 aminoacids (FIG. 1B, bottom, black arrow) specified by the sequence of the polyinker and the first aminoacid of IL-1β and that the leader peptide consists of 19 aminoacids, i.e., the 16 aminoacids of the synthetic oligonucleotide of the hypothetical leader peptide of the killer toxin and the three aminoacids of the polyinker of pEMB18 (Thr, Arg, Gly).

In accordance with the present invention, the biological activity of the secreted recombinant protein was determined by means of the test of stimulation of proliferation of mouse thymocytes.

The results obtained, reported in FIG. 4, show that said protein of 22,000 daltons is endowed with the same biological activity as of natural IL-1β. Cells of E. coli containing the hybrid plasmid YEpsec1-hI1 were filed on Mar. 6th, 1986, with the American Type Center Culture as ATCC 67024.

The pY47 plasmid is built by linking the BamHI-HindIII fragment of 1,700 base-pairs (bp) of G2 plasmid to the BamHI-HindIII fragment of 2,690 bp of plasmid pUC19 (pY42) and removing from pY42 the PstI restriction site in URA3 gene by means of digestion with PstI and treatment with DNA-polymerase I Klenow fragment. The BamHI-HindIII fragment of 1,700 bp of pY47 is isolated and bound to plasmid pEMBL18, previously cut with EcoRI (pY55).

The pY43 plasmid is built by inserting in pEMBL8 the HindIII fragment of 3,560 bp of plasmid pJDB219 containing leu 2-d, STB of 2 μm plasmid and the sequence of the 3' end of FLP of 2 μm plasmid.

The NdeI-StuI fragment of 3,220 bp of pY43 is then linked to HindIII fragment of pY55 to yield the hybrid plasmid pEMBLyex2.

FIG. 1B: In this Figure, the map is reported of the secretion vector YEpsec1 obtained by inserting between the SstI and KpnI restriction sites of pEMBLyex2 the synthetic oligonucleotide.

The sequence reported in the lower part of FIG. 1B corresponds (boldface characters) to the sequence of the hypothetical leader peptide of the gene of the Killer toxin of K. lactis from the initial methionine up to the presumed site of cleavage of endopeptidase (Val-Gln-Gly) (empty arrow), to the junction of this latter (lower-case letters) with the cDNA of interleukin-1β (IL-1β) cloned in said vector (undelined).

The black arrow indicates the experimentally found cleavage site.

Figure 2:
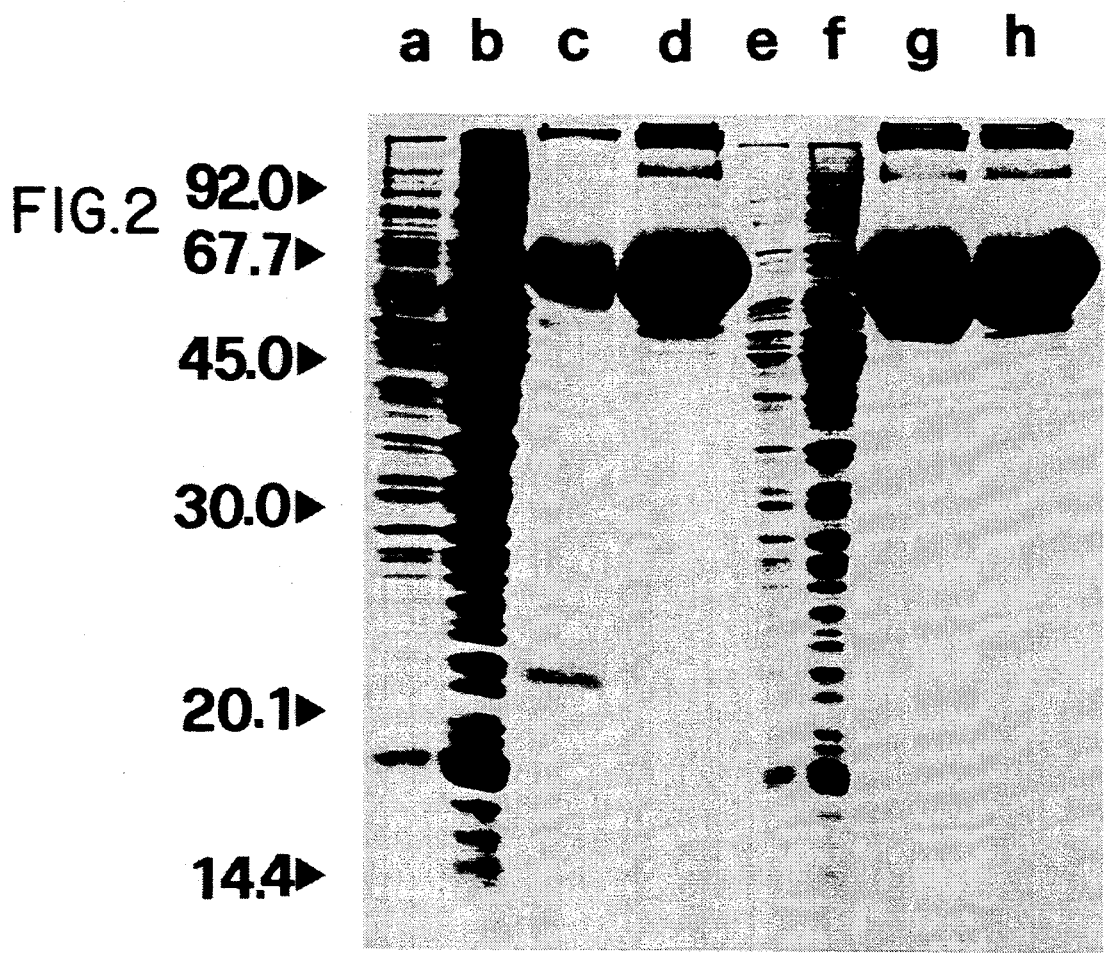

FIG. 2: FIG. 2 reports the electrophoretic analysis on gel of SDS-PAGE polyacrylamide stained with Coomassie of the whole cellular extracts (a and b) and of the supernatants of the cultures (c and d) of ThI1 grown in a complete medium supplemented with 2% of galactose (a and c) or 2% of ethanol (b and d) and of the whole cellular extracts (e and f) and supernatants of cultures of Tsec1 cells (g and h) grown in a complete medium supplemented with 2% of galactose (e and g) or with 2% of ethanol (f and g).

The 67.7-kd band present in all of the supernatants is the bovine seralbumin (BSA) used as the support for protein precipitation.

Figure 3:

FIG. 3: FIG. 3 reports the electrophoretic analysis on SDS-PAGE of the 22,000-dalton protein, before (a) and after (b) the treatment with endoglycosidase H.

Figure 4:
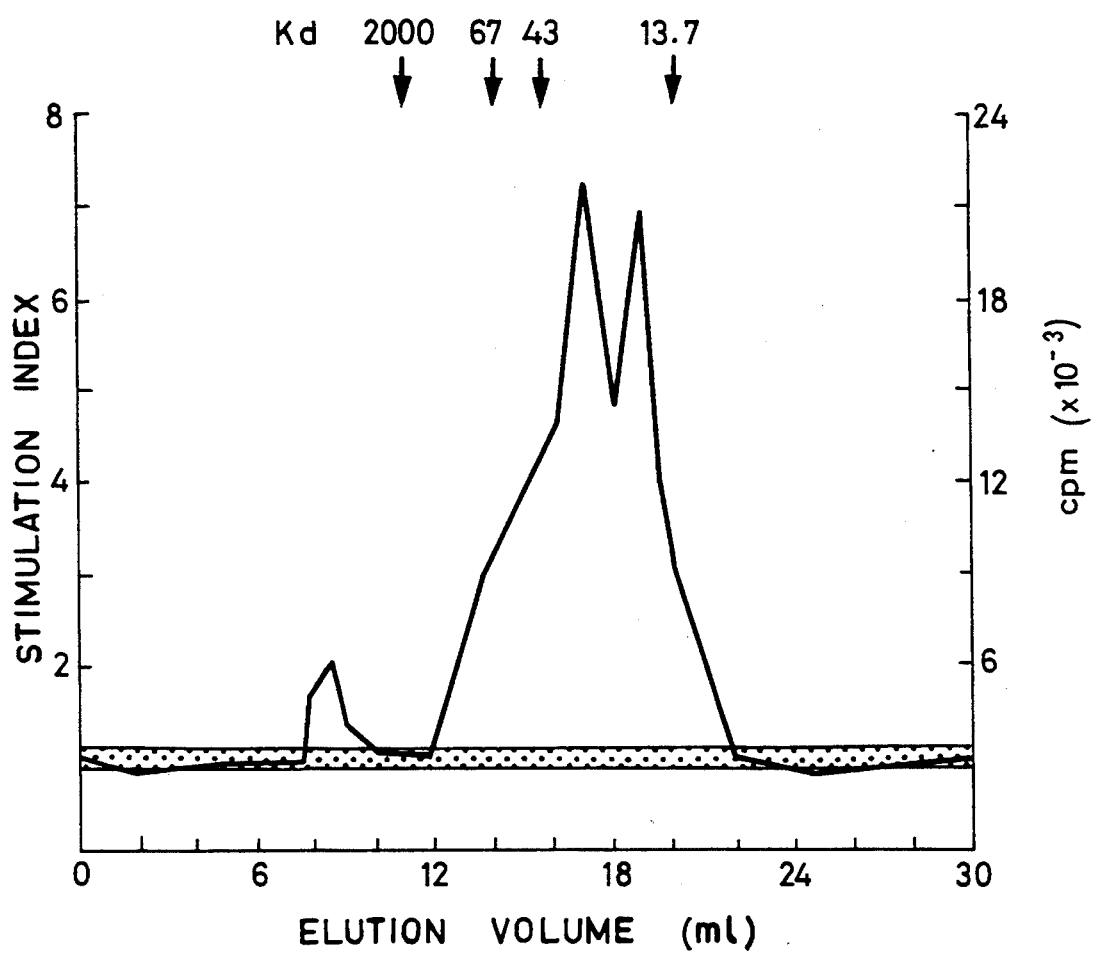

FIG. 4: The chart shows the stimulation of the proliferation of mouse thymocytes by means of the supernatant fraction obtained from a culture of ThI1 grown in a medium with galactose. Abscissae: Volume (ml) of elution from the Sephacryl-S200 column. Ordinates: Incorporation of [$^3$H]-thymidine by the mouse thymocytes.

The incorporation of [$^3$H]-thymidine by the mouse thymocytes stimulated by phytohaemagglutinin (PHA) is shown in the dotted area. The standard molecular weights are indicated by the arrows. Each point is the average of three determinations with SEM<10%.

EXAMPLE 1

Figure 1A:
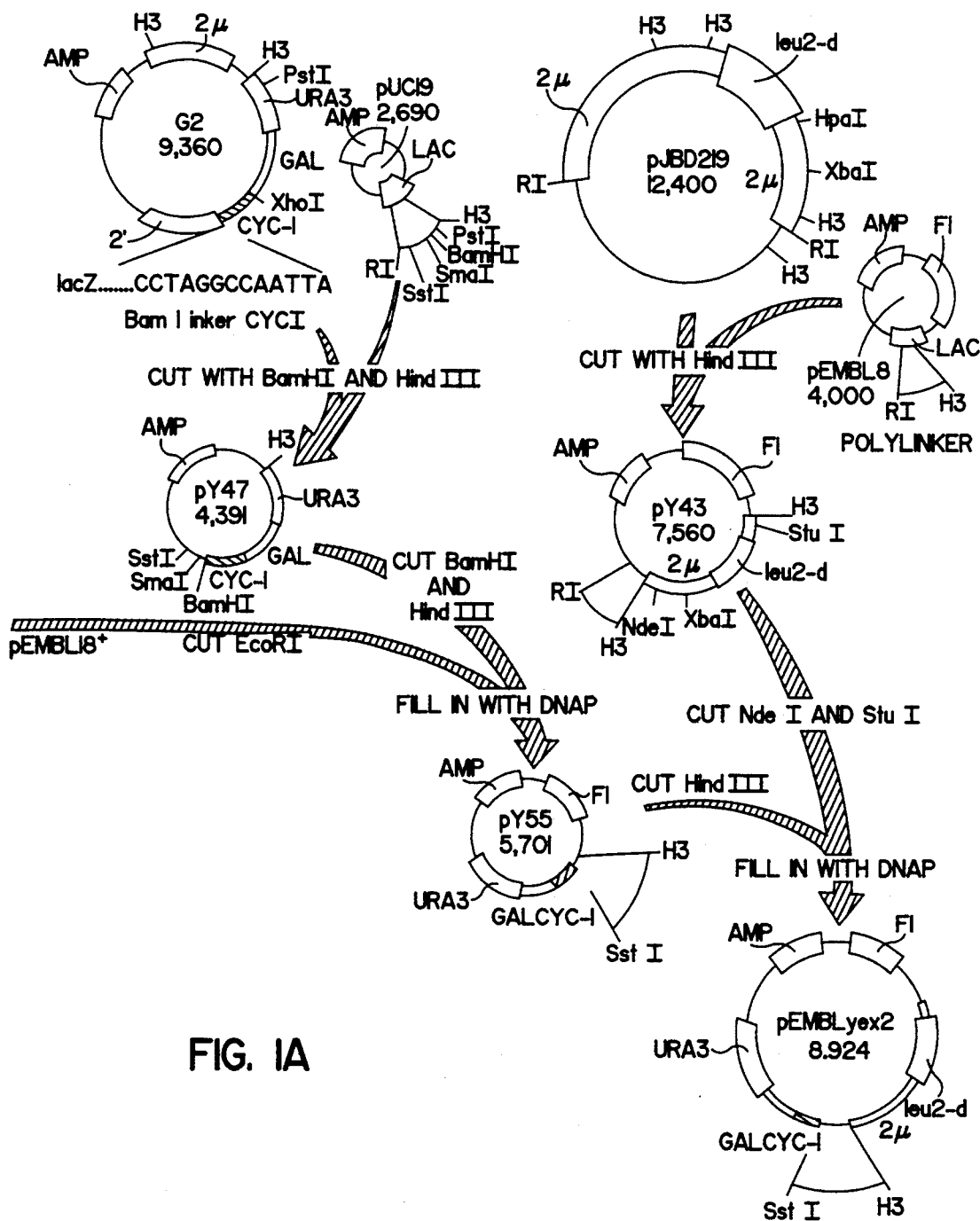
FIG. 1A The structure is schematically shown of the expression pEMBLyex2 plasmid vector and of the secretion YEsec1 vector.

Building of the Expression and Secretion YEpsec1 Vector (FIGS. 1a and 1b)

2 μg of G2 plasmid and 2 μg of pUC19 plasmid are respectively cut with 2 units (U) of restriction enzyme BamHI and HindIII (Biolabs) in 20 μl of phosphate buffer (pH 7.4), under the operating conditions as suggested by the supplier. The digestion reaction is then stopped at 65° C. for 10 minutes, and the resulting digestion mixtures are charged on low-liquifying-point 0.6% agarose gel (BRL) and run at 110 V for 3 hours.

The bands respectively corresponding to the BamHI-HindIII fragment of 1,700 base-pairs (bp) of G2 and BamHI-HindIII fragment of 2,690 bp of pUC19 are cut and linked in the presence of T4 DNA ligase, without isolating them from agarose, as described by Crouse et al., in Methods in Enzymology, Vol. 101, pages 78–89, 1983).

10 μl of the so-obtained ligase mixture are used for transforming cells of E. coli JM 101 (BRL), rendered competent according to the method as described by D.A. Morrison in Enzymol., Vol. 68, 326 (1979).

The transformants are selected on slabs of LB agar (DIFCO), to which 50 μg/ml of Ampicillin were added.

From one of the so-obtained positive clones, the pY42 plasmid, of 4,391 bp, is extracted. Said plasmid is cut with 2 U of PstI (BRL) and is treated with polymerase (Klenow-Boehringer) for 5 minutes at 37° C., for the purpose of eliminating the PstI restriction site in URA 3 gene.

The mixture is then treated with T4 DNA ligase in 1 mM ATP, 10 mM dithiothreitol, 20 mM tris-HCl, 10 mM MgCl$_2$ buffer, at 15° C., for 16 hours and to an end concentration of 150 μg/ml of DNA.

The whole ligase mixture is then used for transforming competent cells of E-coli JM 101, as reported above.

From one of the positive clones, pY47 plasmid is isolated. This plasmid is cut with BamHI and HindIII, as previously reported, and the BamI-HindIII fragment of 1,700 bp of pY47 is linked to the pEMBL18 plasmid previously cut with EcoRI and treated with polymerase. The ligase mixture is then used for transforming component cells of E. coli JM 101. From one of the positive clones, the pY55 plasmid of 5,701 bp is isolated.

The analysis of hybridization on cellulose filter shows that said plasmid is constituted by pEMBL18 and by the BamHI-HindIII fragment of 1,700 bp. 2 μg of pJBD 219 (J. D. Beggs, Nature, 275, 104–109 (1978) and 2 μg of pEMBL8 (L. Dente et al., DNA Cloning, Vol. 1, IRL Press, London, U.K., pages 101–107 (1985) are respectively cut with 2 U of HindIII (Biolabs).

The digestion mixture is then charged on 0.6% agarose gel and run at 110 Volt for 3 hours. The band corresponding to the HindIII fragment of 3,560 bp of JBD219 (Baggs J.D., Nature 275, 104–109, 1978) is cut and added to the digestion mixture of pEMBL8 in the presence of T4 DNA ligase.

10 μl of ligase mixture is then used for transforming competent cells of E. coli JM 101 and from one of the positive transformants the pY43 plasmid of 7,560 bp is isolated.

2 μg of pY43 is digested with 2 U of NdeI and 2 U of StuI (BRL).

5 μl of said digestion mixture is added to 5 μl of a digestion mixture obtained by cutting pY55 with HindIII, in the presence of T4 DNA ligase, by operating as above.

The positive clones are identified by hybridization using as the probe the NdeI-StuI fragment of labeled pY43. By operating in such way, the hybrid pEMBLyex2 plasmid of 8,924 bp is isolated, which contains the gene coding for Ampicillin resistance, the origin of replication of F1 phage, the gene of uracyl 3 (URA 3) and the leucine 2-d gene of S. cerevisiae and the hybrid promoter derived from G2 followed by the polyinker of pEMBL18.

15 μg of pEMBLyex2 is cut with 5 U of SstI and partially with 1 U of KpnI. The digestion mixture is then charged on 0.6% agarose gel and run at 110 V for 3 hours.

The band corresponding to the highest-molecular-weight fragment is separated and linked with the oligonucleotide:

```
     1   2   3   4   5   6   7   8   9  10  11  12  13  14  15  16
   C ATG AAT ATA TTT TAC ATA TTT TTG TTT TTG CTG TCA TTC GTT CAA GGT AC
  TC GAG TAC TTA TAT AAA ATG TAT AAA AAC AAA AAC GAC AGT AAG CAA GTT C
``` synthesized by using an Applied Biosystems 380A synthesizer.

The ligase mixture is also used for transforming competent cells of E. coli HB101 (F$^-$ hsdS20 rec A13 ara-14 proA2 lacY1 galK2 rpsL20 xy15 met-1 supE44).

The transformants are then selected for Ampicillin-resistance as reported above.

From a positive clone, YEpsec1 plasmid is finally isolated (FIG. 1B).

EXAMPLE 2

Building of Hybrid YEpsec1-hI-1β plasmid

Cells of THP1 cellular line, grown in RPMI to a density of 10$^6$ cells/ml, are stimulated for 4 hours with TPA 12-0-tetradecanoylphorbol-13-acetate (0.1 μg/ml). Total RNA is extracted from such cells according to the method as described by Maniatis et al., Molecular Cloning: A Laboratory Manual, Cold Spring, Harbor, 1982, 194–195.

RNA is run on a column of oligo-dT and is fractionated on a saccharose gradient (5–20%) in 20 mM sodium acetate (pH 5.5). The fractions are hybridized with a synthetic probe of 55 bp corresponding to the last 18 codons of the sequence of the gene of interleukin-1β (IL-1β) (Auron et al., P.N.A.S. 81, 7908–7011, 1984).

The positive fractions are used for preparing the cDNA's according to as descriped by Gruber et al. in Gene 25, 263–269 (1983).

The above described probe is used for identifying the recombinant clones.

The plasmidic DNA of one of these clones is used for isolating the Sau3A partial fragment of 600 bp containing the cDNA of IL-1 (Auron, L. cit.). Such fragment is inserted in BamHI site of YEPsec1 plasmid situated immediately downstream the synthetic oligonucleotide for obtaining the hybrid YEpsec1-hI-1β plasmid. This latter was used for transforming the cells of *E. coli* and these cells were filed on Mar. 6, 1986, with the American Type Center Culture with the access number ATCC 67024.

After approximately 40 hours, the electrophoretic analysis of the supernatants is carried out, for the purpose of determining the presence of IL-1β.

The cellular extracts are prepared by mechanical cold-breakage of the cells by means of small glass balls, for 2 minutes inside a vortex, centrifuging of the cellular suspension at 10,000 rpm for 15 minutes, and then dilution of the so-clarified liquid in a buffer of 2% SDS, 10% glycerol, 5% mercaptoethanol, and 62.5 mM Tris-HCl, pH 6.8.

The supernatants are prepared on the contrary by centrifuging the cell culture at 4,000 rpm for 5 minutes and filtering the supernatant on sterile filters of 0.45 μm Millipore.

The filtrate is then stored at 0° C. and is subsequently analysed for determining IL-1β.

To 1.8 ml of said filtrate, bovine seralbumin (BSA) by SIGMA, to an end concentration of 100 μ/ml, and 0.2 ml of trichloroacetic acid (TCA) are then added.

The mixture is then kept at −20° C. for 30 minutes and is centrifuged at 10,000 rpm for 15 minutes. The precipitate is washed and re-suspended in 25 μl of buffer (2% sodium dodecyl sulphate, 10% glycerol, 5% mercaptoethanol, 62.5 mM Tris-HCl, pH 6.8).

The obtained solution is maintained at boiling temperature for 3 minutes, and is then charged on 15% acrylamide gel, prepared as described by Laemmli, Nature (1970) 227, 680–684, and is run at 150 V for 5 hours.

For control purposes, the same analyses are carried out on the cellular extracts, and on the supernatant of ThI1 and Tsec1 cells cultivated in a complete medium, wherein galactose was replaced by ethanol, which, in the yeast, does not activate the expression of the gene which codes for human IL-1β.

| Ala | Pro | Val | Arg | Ser | Leu | Asn | Cys | Thr | Leu | Arg | Asp | Ser | Gln |
|---|---|---|---|---|---|---|---|---|---|---|---|---|---|
| Gln | Lys | Ser | Leu | Val | Met | Ser | Gly | Pro | Tyr | Glu | Leu | Lys | Ala |
| Leu | His | Leu | Gln | Gly | Gln | Asp | Met | Glu | Gln | Val | Val | Phe | Ser |
| Met | Ser | Phe | Val | Gln | Gly | Glu | Glu | Ser | Asn | Asp | Lys | Ile | Pro |
| Val | Ala | Leu | Gly | Leu | Lys | Glu | Lys | Asn | Leu | Tyr | Leu | Ser | Cys |
| Val | Leu | Lys | Asp | Asp | Lys | Pro | Thr | Leu | Gln | Leu | Glu | Ser | Val |
| Asp | Pro | Lys | Asn | Tyr | Pro | Lys | Lys | Lys | Met | Glu | Lys | Arg | Phe |
| Val | Phe | Asn | Lys | Ile | Glu | Ile | Asn | Asn | Lys | Leu | Glu | Phe | Glu |
| Ser | Ala | Gln | Phe | Pro | Asn | Trp | Tyr | Ile | Ser | Thr | Ser | Gln | Ala |
| Glu | Asn | Met | Pro | Val | Phe | Leu | Gly | Gly | Thr | Lys | Gly | Gly | Gln |
| Asp | Ile | Thr | Asp | Phe | Thr | Met | Gln | Phe | Val | Ser | Ser | | |

EXAMPLE 3

Expression and Secretion of Interleukin-1β from cells of *S. cerevisiae*

Cells of *S. cerevisiae* S150-2B (Leu 2-3 Leu 2-112 ura 3-52 trp 1-289 his 3-1 cir+) are respectively transformed with the hybrid YEpsec-hI1β plasmid (*S. cerevisiae* ThI1) and with the YEsec1 vector (*S. cerevisiae* Tsec1) according to the method by Rothstein R, (1985) in Glover, D.M. (Ed.), DNA Cloning, IRL Press, London, Vol. II, pages 45–46.

The so-transformed cells are cultivated inside Erlenmeyer flasks of 2 L of capacity, containing 1 of a medium having the following composition:

| | |
|---|---|
| yeast extract (DIFCO) | 1% |
| peptone (DIFCO) | 1% |
| galactose (Merck) | 2% |
| KH$_2$PO$_4$ | 0.3% |
| H$_2$O | 1 Liter |
| (pH 5.5) at 200 rpm, and at 30° C. | |

The gel-electrophoretic analyses are carried out by using as the control standard for the molecular weights 1 μl of Low Molecular Weight by BIORAD (14,400–92,000 daltons).

The results reported in FIG. 2 show the presence, in correspondence of 22,000 daltons, of a band in the filtrate from the culture of *S. cerevisiae* ThI1 only. By assuming that the protein secreted by ThI1 is IL-1β, its molecular weight should be of about 17,000, and not 22,000, daltons, and the discrepancy in the molecular weight should hence be due to the presence of oligosaccharides bound to the end amino group of the protein. The digestion of said protein with endoglycolase H enzyme shows in fact the disappearance of the band of 22,000 daltons, and the appearance of a new band of approximately 17,000 daltons (FIG. 3).

This result is confirmed by means of the inhibition of the glycosylation in vivo by means of tunicamycin.

The supernatants of cultures of ThI1 grown in a medium containing galactose and tunicamycin at a concentration higher than 0.5 μg/ml produce in fact only the protein of 17,000 daltons.

For the purpose of verifying the identity of said protein, and the correct secretion processing, the first aminoacids are analysed according to the method by Edman, reported by Hewick et al in J. Biol. Chem., 256, 1990-1997 (1981). The results obtained confirm the expected sequence for IL-1β. None of the aminoacids coded by the polyinker is found at the amino end of the protein, thus suggesting that the cutting of the leader peptide takes place between the last one of the three aminoacids coded by the sequence of the polyinker and the first aminoacid of IL-1β (FIG. 1B).

The biological activity of the so-secreted protein is tested on the supernatant obtained from the culture of ThI1 cells by means of the analysis of thymocyte proliferation, as described by Gerg et al. in Cell. Immunology, Vol. 64, 293-303 (1984).

In practice, the supernatant is concentrated by means of ultrafiltration and is charged on a Sephacryl-S 200 column (30×1 cm) equilibrated with 0.15M NaCl at a flowrate of 1 ml/minute and fractions of 0.5 ml, with a molecular weight of from 20,000 to 22,000 are collected and analysed as follows.

$6 \times 10^5$ thymocytes obtained from C3H/HeJ mice of 4-8 weeks are introduced in wells of microslabs, and are contacted with 0.2 ml of scalar solutions of the fractions in RPMI 1640 medium, in the presence of 5% fetal seralbumin (FBS, Hy-Clone, Sterile Systems), 50 μg/ml of gentamycin sulphate (Sigma), 25 mM HEPES, 2 mM L-glutamin and $1.25 \times 10^{-5}$ M of 2-mercaptoethanol.

The cultures are labeled with 1 μCi/well of 3HdThd thymidine and are maintained at 37° C. for 16-18 hours. At the end of this time, the cells are recovered on fiberglass filters and analysed by spectrometry, for the purpose of determining the incorporated radioactivity. The proliferation is measured as counts per minute (cpm), and is expressed as a "proliferation index", i.e., the ratio of the PHA+fraction cpm to the control cpm (i.e., PHA without fraction). The results as shown in FIG. 4 indicate a high proliferation in correspondence of the fraction with a molecular weight of about 22,000 daltons.

We claim:

1. A cloning vector for expression and secretion in yeasts, containing the inducible promoter GAL-CYC, the FLP termination signal sequence of transcription recognized by yeasts and one secretion signal sequence consisting of:

ATG AAT ATA TTT TTT ATA TTT TTG TTT TTG CTG
1    2    3    4    5    6    7    8    9    10   11

TCA TTC GTT CCA GGT ACC CGG GGA.
12   13   14   15   16   17   18   19

2. The cloning vector of claim 1, wherein the secretion signal sequence encodes a 19-amino acid peptide having the following amino acid sequence: Met Asn Ile Phe Tyr Ile Phe Leu Phe Leu Leu Ser Phe Val Gln Gly Thr Arg Gly.

3. The cloning vector of claims 1 or 2 obtained by a process consisting of the steps of:
   (a) building the expression vector pEMBLyex2 containing the leu2-d gene, the replication origin of the F1 phage, the gene coding for resistance to ampicillin, the gene uracil-3, the inducible hybrid promoter GAL-CYC derived for G2 and the polylinker of pEMBL18;
   (b) digesting the pEMBLyex2 with the restriction enzymes SstI and KpnI which cut in the restriction siste of the polylinker;
   (c) inserting in the restriction sites SstI and KpnI of the plasmid obtained in stage (b) the synthetic nucleotide which has the following sequence:

```
    1   2   3   4   5   6   7   8   9   10  11  12  13  14  15  16
  C ATG AAT ATA TTT TAC ATA TTT TTG TTT TTG CTG TCA TTC GTT CAA GGT AC
 TC GAG TAC TTA TAT AAA ATG TAT AAA AAC AAA AAC GAC AGT AAG CAA GTT C
```

(d) isolating the resulting expresion and secretion vector.

4. A cloning vector for expression and secretion in yeasts of interleulin-1β, containing the inducible promoter GAL-CYC, the FLP termination signal sequence of transcription recognized by yeast and one secretion signal sequence consisting of:

ATG AAT ATA TTT TTT ATA TTT TTG TTT TTG CTG
1    2    3    4    5    6    7    8    9    10   11

TCA TTC GTT CCA GGT ACC CGG GGA.
12   13   14   15   16   17   18   19

5. S. Cerevisiae containing a hybrid plasmid that expresses and secretes human interleukin 1β, said hybrid plasmid comprising a heterologous gene coding for said human interleukin 1β and being under the control of the promoter, secretion signal sequence, and termination sequence contained in the cloning vector according to claims 1 or 2.

6. An E. coli cell which secretes human interleukin 1β, said cell containing the hybrid plasmid YEpsec1-hI-1β, deposited as ATCC number 67024.

7. A hybrid plasmid contained in a usable form of S. cerevisiae to express and secrete human interleukin 1β which is YEpsec1-hI-1β.

* * * * *